United States Patent [19]

Salem et al.

[11] Patent Number: 4,909,260

[45] Date of Patent: Mar. 20, 1990

[54] PORTABLE BELT MONITOR OF PHYSIOLOGICAL FUNCTIONS AND SENSORS THEREFOR

[75] Inventors: Robert J. Salem, New Milford; George H. Holley, South Norwalk, both of Conn.

[73] Assignee: American Health Products, Inc., Orange, Calif.

[21] Appl. No.: 128,144

[22] Filed: Dec. 3, 1987

[51] Int. Cl.⁴ .................................................. A61B 5/08
[52] U.S. Cl. ..................................... 128/721; 128/671; 310/331
[58] Field of Search ............... 128/721, 671, 700, 903, 128/644; 340/573; 310/331

[56] References Cited

U.S. PATENT DOCUMENTS

| | | | |
|---|---|---|---|
| 3,187,300 | 6/1965 | Brate | 340/10 |
| 3,268,845 | 8/1966 | Whitmore | 338/47 |
| 3,530,851 | 9/1970 | Geschickter | 128/644 |
| 3,749,948 | 7/1973 | Morris | 310/331 X |
| 3,782,368 | 1/1974 | Riebold | 128/721 |
| 3,938,507 | 2/1976 | Scmoff et al. | 128/698 |
| 3,940,974 | 3/1976 | Taylor | 73/88.5 R |
| 4,121,575 | 10/1978 | Mills et al. | 128/644 |
| 4,122,843 | 10/1978 | Zdrojkowski | 128/644 |
| 4,129,125 | 12/1978 | Lester et al. | 128/671 |
| 4,169,462 | 10/1979 | Strube | 128/721 |
| 4,185,621 | 1/1980 | Morrow | 128/672 |
| 4,356,825 | 11/1982 | Veth | 128/630 |
| 4,443,730 | 4/1984 | Kitamura et al. | 310/330 |
| 4,494,553 | 1/1985 | Sciarra et al. | 128/721 |
| 4,576,179 | 9/1986 | Manus et al. | 128/671 |

FOREIGN PATENT DOCUMENTS

| | | | |
|---|---|---|---|
| 1492875 | 11/1977 | United Kingdom | 128/721 |
| 2181555 | 4/1987 | United Kingdom | 128/721 |

Primary Examiner—Lee S. Cohen
Attorney, Agent, or Firm—St. Onge Steward Johnston & Reens

[57] ABSTRACT

A portable belt-type monitor of body functions such as the heart and breathing is described formed of a plurality of articulated, distributed modules containing EKG sensors, a respiration sensor, circuitry including a microprocessor for sensing alarm conditions, a transmitter for sending alarm conditions to a remote receiver and a battery to drive the various circuits. A respiration sensor is described wherein tension changes in the belt due to breathing are transformed into opposing forces directed transversely to the belt and which cooperate to produce a reliable, sensitive detection of respiratory activities. The belt can be conveniently worn with reliable EKG sensing during normal body activities. A processor program is described whereby these body functions are monitored with alarm being generated when these functions exceed preset limits while preserving sufficient functional performance data when an alarm occurs.

19 Claims, 6 Drawing Sheets

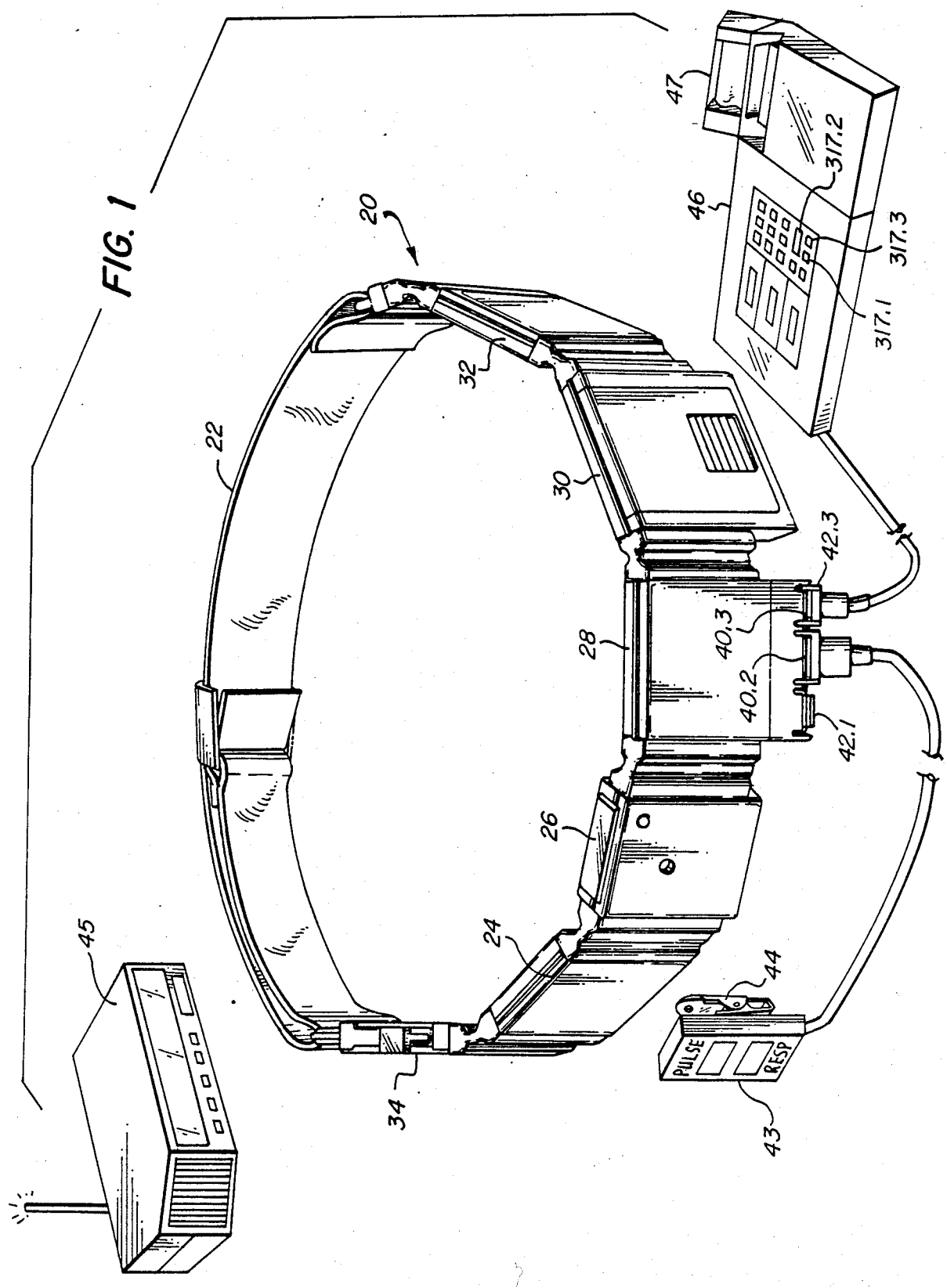

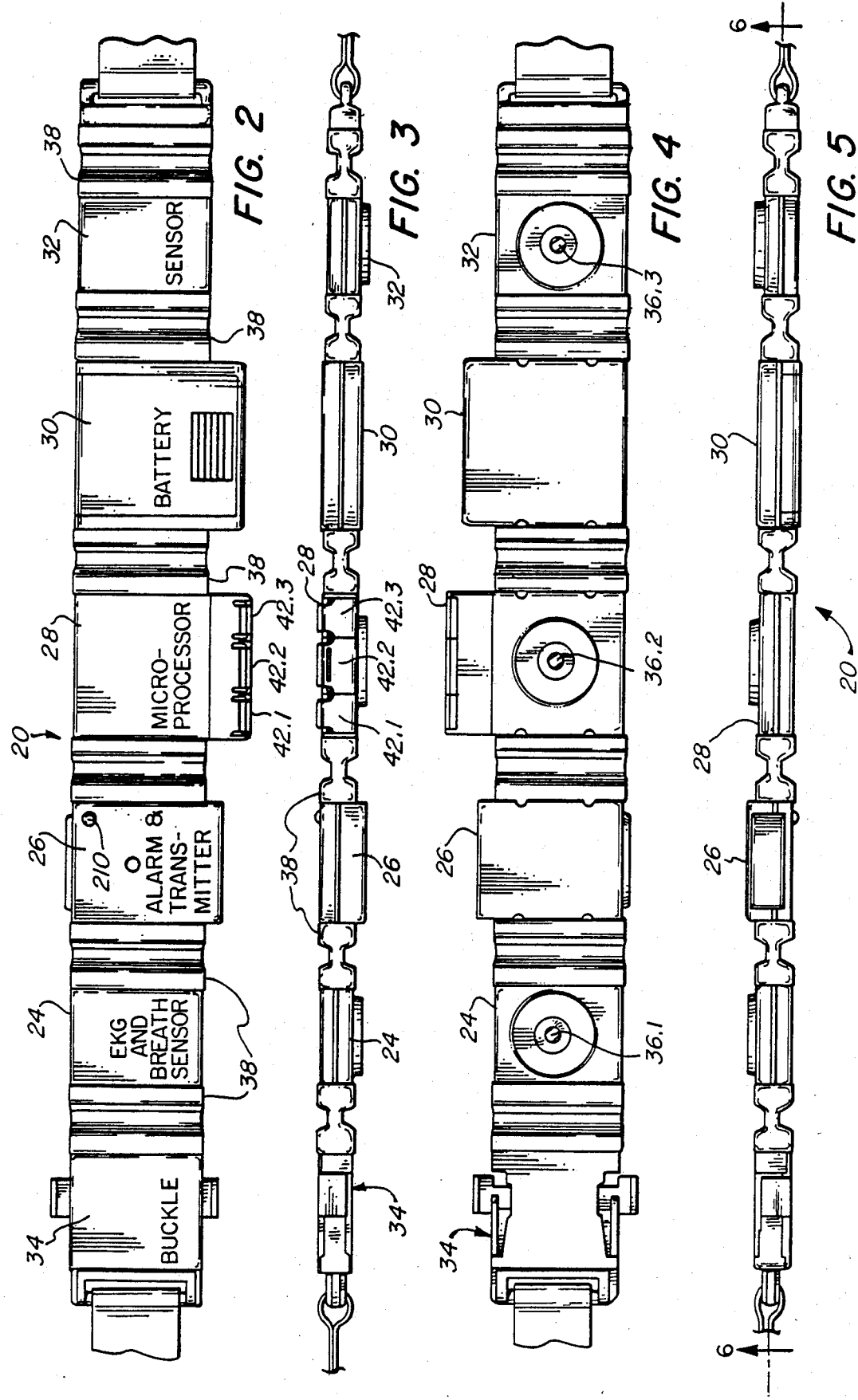

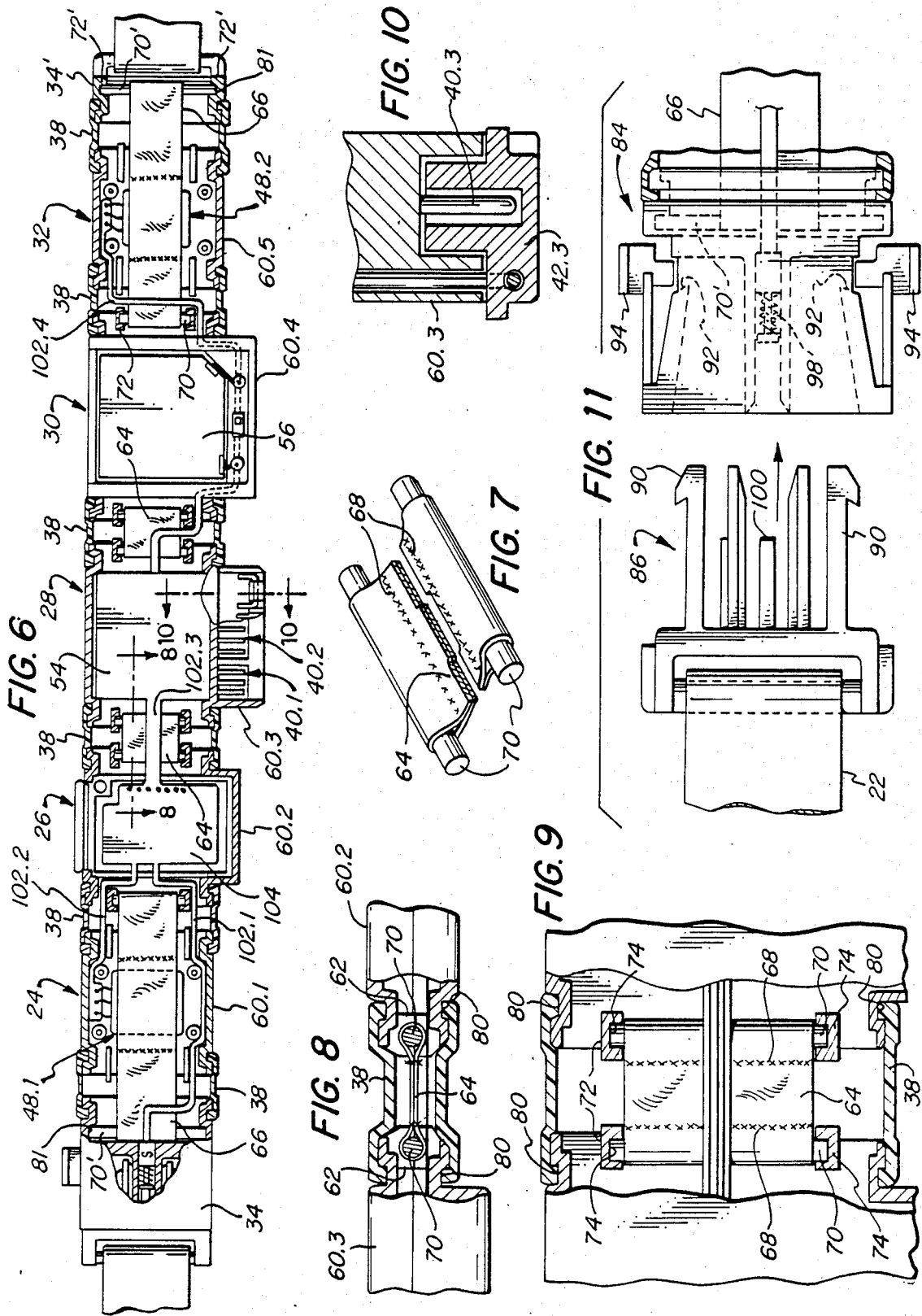

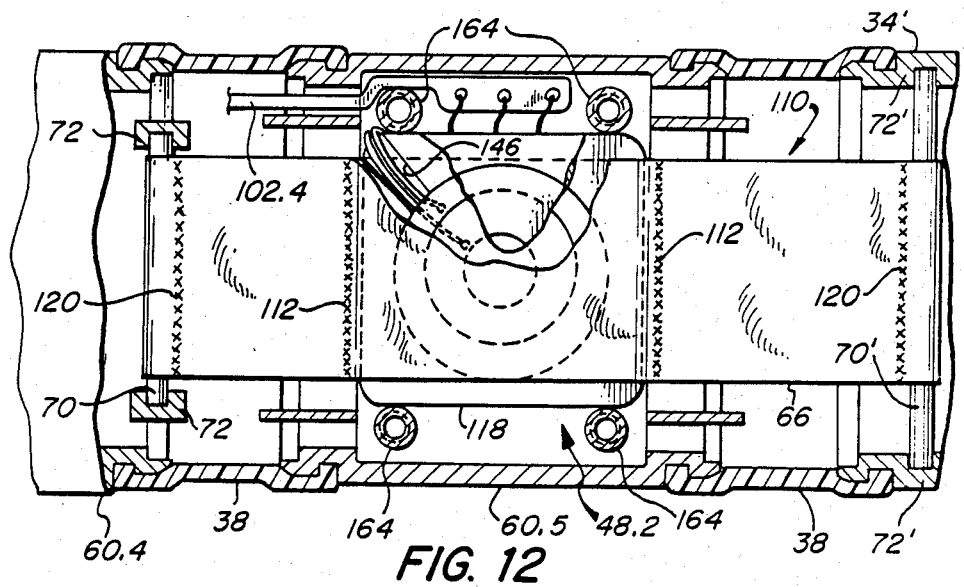
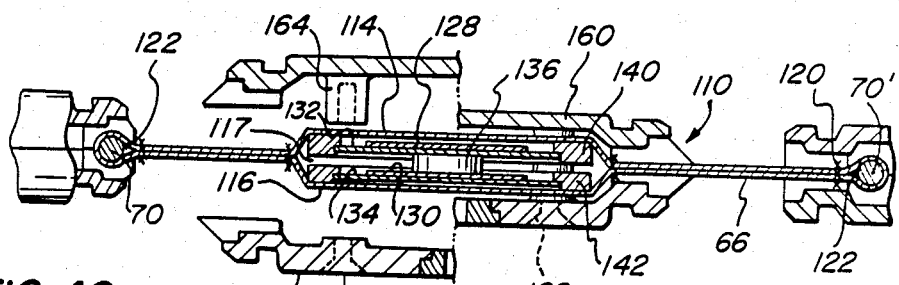
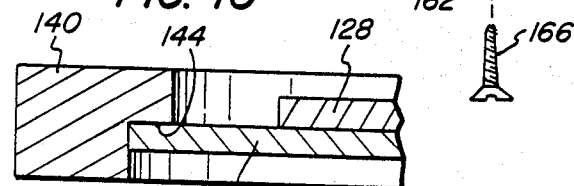
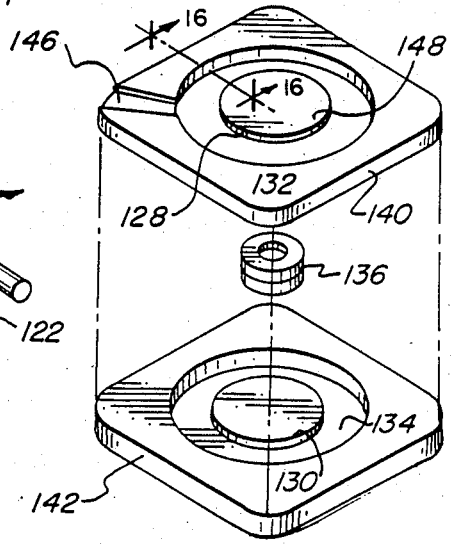
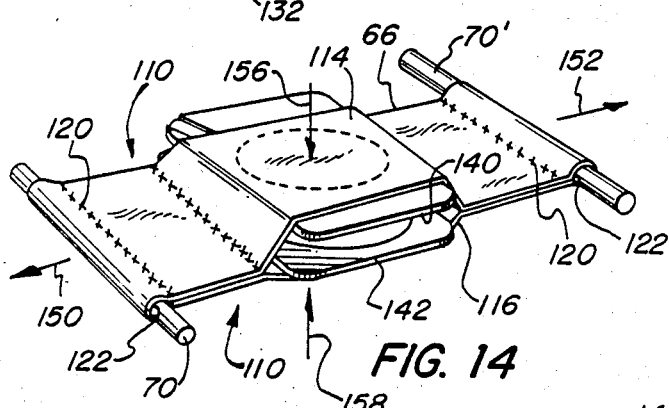

PORTABLE BELT MONITOR OF PHYSIOLOGICAL FUNCTIONS AND SENSORS THEREFOR

FIELD OF THE INVENTION

This invention relates to a device for monitoring physiological functions such as breathing and heart rate. More specifically, this invention relates to a belt that can be worn to sense breathing and/or heart rate and produces an alarm signal when dysfunctions are detected.

BACKGROUND OF THE INVENTION

Belts for monitoring body vital signs such as respiratory and cardiac activity are known. One such belt is described and shown in U.S. Pat. No. 3,268,845 and uses a variable resistance transducer. Another is shown in U.S. Pat. No. 4,494,553 and describes the use of multiple inductance coils. Others are shown in U.S. Pat. Nos. 4,121,575, 4,185,621, 3,782,368, 4,122,843 and 3,530,851.

The use of piezoelectric transducers for sensing respiratory function are well-known. See for example, U.S. Pat. Nos. 4,576,179, 3,782,368, 4,169,462, 4,185,621 and 4,443,730. These typically describe the use of piezo transducers that are sensitive to body breathing motions as well as impacts or forces incident from various directions.

In some devices piezoelectric transducers are used wherein a pair of piezo elements are connected so as to compensate either for pressure changes when temperature is to be sensed or for temperature when pressure is to be sensed. See for example, U.S. Pat. Nos. 3,940,974 and 3,187,300.

Various portable respiratory sensors that communicate with base units through rf communication links have been described, see U.S. Pat. No. 3,938,507. Systems have also been described for monitoring physiological parameters with devices that employ a microprocessor as in U.S. Pat. No. 4,356,825.

SUMMARY OF THE INVENTION

With a physiology monitor in accordance with the invention, parameters such as respiratory rate and/or cardiac functions can be sensitively and reliably monitored with circuits mounted in a belt and powered by a battery. Alarm conditions are sensed and signals indicate thereof are transmitted to a remotely-located base unit.

In one monitor in accordance with the invention a stretchable elongate belt is employed which is sized to fit around the torso of a body. The belt undergoes tension changes attributable to expansion and contraction along the elongate axis of the belt during breathing. A sensor holder is interposed in the belt in such a way so as to convert part of an elongate tension change into opposing forces operative along a sensing axis that is directed generally transverse to the belt. A pressure transducer is placed in the holder with an orientation so as to preferentially respond to these transverse opposing forces to produce an electrical breathing signal.

With a monitor in accordance with the invention, breathing activity can be detected substantially independent of body motions. For example, when a belt is placed around an infant, he or she can move around, roll over onto the sensor and subject the belt to normal body movements while still being able to reliably detect breathing. A belt monitor of this invention is, therefore, particularly useful for sensing apnea conditions with a minimum of false alarms.

Although various transducers could be employed, a preferred transducer or sensor is formed with a pair of piezoelectric planar elements. These are placed in parallel with each other with a spacer between them. The elements respond to bending forces that are transverse to their planes so as to produce electrical signals. The elements are so connected to each other that their respective electrical outputs complement each other in response to oppositely directed bending forces and cancel each other in response to a unidirectional force. Such cancellation can arise from a unidirectional force produced by a physical impact or from a temperature change.

The piezo elements are placed between the walls of a collapsible pocket in the sensor holder. The pocket is so aligned that its opposite walls lie generally in parallel with the tension forces in the belt at the sensor. As the belt undergoes tension changes as a result of breathing, the walls of the pocket are moved towards or away from each other, thus applying variable oppositely directed bending forces to the piezo elements. The latter then generate a useful signal that is detected and used to monitor breathing functions.

With such sensor structure, a sensitive detection of respiratory functions is obtained, yet without responding to other physical activities. When a patient rolls over in his sleep or accidentally impacts the sensor, the directionality of the sensor minimizes signal responses. This aspect is further enhanced by enclosing the piezo elements and holder inside a rigid housing while keeping the holder anchored in "series" with the belt.

When a sensitive respiratory monitor in accordance with the invention is used, belt changes attributable to heart beats can also be detected. The heart beat portions are separated by applying the sensor signal to an appropriate filter capable of separating higher frequency heart signals from lower frequency respiratory signals.

One physiology function monitor in accordance with the invention is formed of a plurality of individual generally flat modules that are interconnected in an articulated fashion by flexible but non-stretchable webs that enable the modules to conform to the body. Electrical conductors lie along the web to interconnect the modules. One module contains a replaceable battery, another the respiratory sensor, and still others appropriate circuitry needed to operate the monitor and a battery. Receptacles are provided to receive replaceable conventional cardiac sensors that are used to obtain EKG measurements. Flexible sealing elements are used between adjacent modules to prevent intrusion of foreign materials while preserving an articulated monitor belt.

With such a monitor belt, EKG electrodes can be applied to the modules while applying the EKG signals to appropriate processing circuitry in a nearby module with short wires so as to reduce noise and signal interference. As a result reliable EKG detection is achieved even during extensive normal body movements and activities.

With a monitor belt in accordance with the invention, a recent history of operating conditions is preserved in a non-volatile memory. This assures that a physician can analyze a patient's physiology during critical moments before a serious dysfunction occurs. Performance of the operation of the monitor can be verified and analog measurements are available for analysis in a convenient manner.

It is, therefore, an object of the invention to provide a physiology monitor that is portable, dependable in operation with few false alarms attributable to normal body movements and sensitive in obtaining measurements during normal body activities. It is a further object of the invention to provide a dependable portable monitor of respiratory and heart activities. It is a further object of the invention to provide a pressure sensor.

These and other advantages and objects of the invention can be understood from the following detailed description of one portable respiratory and heart rate monitor in accordance with the invention as shown in the drawings.

BRIEF DESCRIPTION OF THE DRAWINGS

FIG. 1 is a perspective view of a belt monitor in accordance with the invention;

FIG. 2 is a front view in elevation of the modular portion of the belt monitor of FIG. 1;

FIG. 3 is a bottom view of the belt monitor as shown in FIG. 1;

FIG. 4 is a rear view in elevation of the belt monitor as shown in FIG. 1;

FIG. 5 is a top view of the belt monitor as shown in FIG. 1;

FIG. 6 is a front partially broken away and partial section view of the module portion of the belt monitor of FIG. 1;

FIG. 7 is a perspective view of a connecting web used to interconnect modules in the belt monitor;

FIG. 8 is a section view of the connecting web taken along the line 8—8 in FIG. 6;

FIG. 9 is a top section view of a connecting web portion as used along the line 8—8 in FIG. 6;

FIG. 10 is a section view of a connector port taken along the line 10—10 in FIG. 6;

FIG. 11 is an exploded top view of the clasp portion of the belt monitor shown in FIG. 1;

FIG. 12 is an enlarged top section partially broken away view of a respiratory sensor in accordance with the invention as employed in the belt monitor of FIG. 6;

FIG. 13 is a section, partially exploded view of the respiratory sensor of FIG. 12;

FIG. 14 is a perspective view of respiratory sensing elements and a sensor holder used in the belt monitor of FIG. 6;

FIG. 15 is an exploded view of the sensing elements used in the respiratory sensor of FIG. 12;

FIG. 16 is a section view of a portion of the respiration sensor taken along the line 16—16 in FIG. 15;

DETAILED DESCRIPTION OF DRAWINGS

Figure 17:
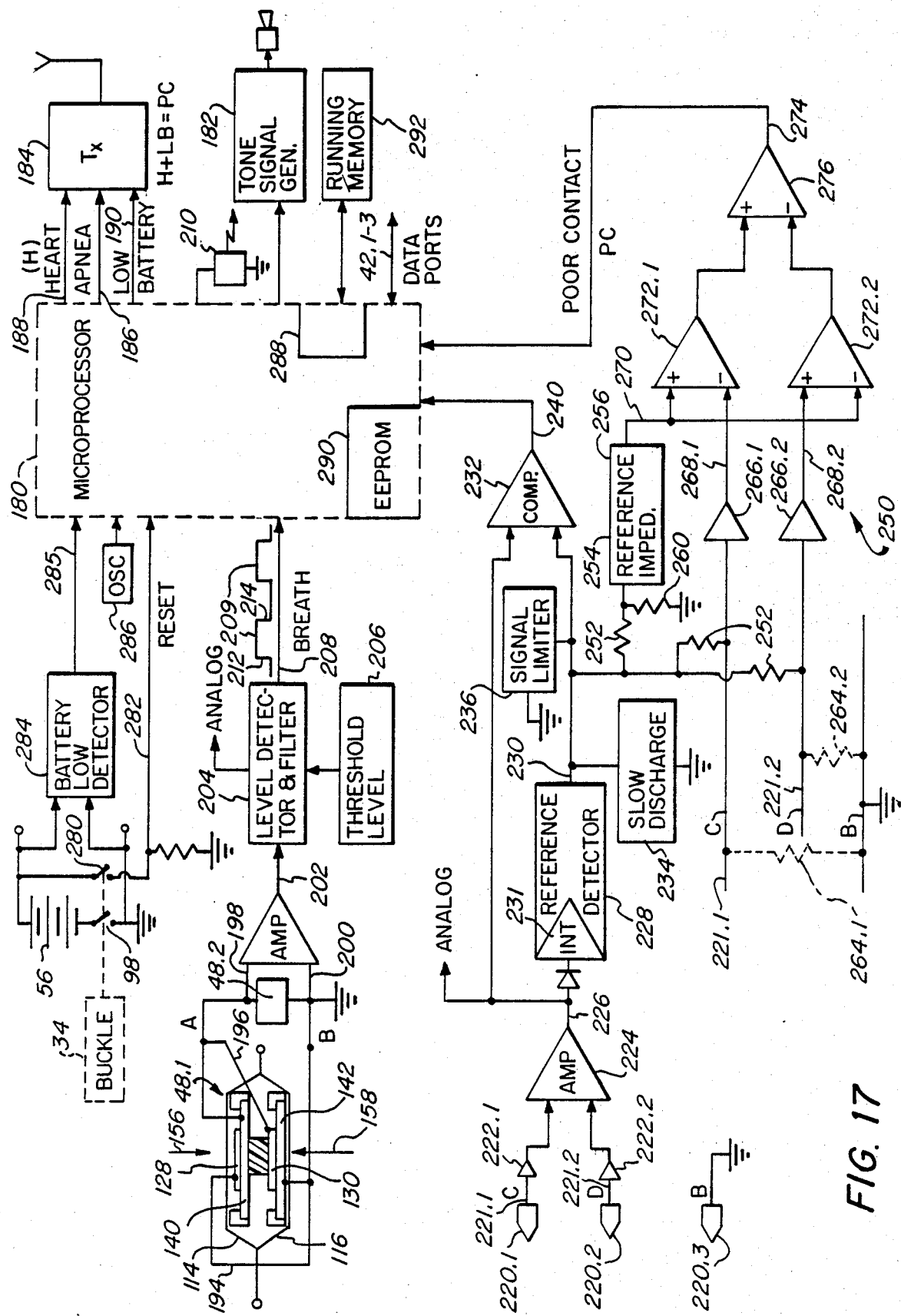
FIG. 17 is a block diagram of an electronic circuit used to monitor physiological functions and transmit these to a base unit.

With reference to FIGS. 1 through 5, a physiology monitor 20 in accordance with the invention is shown formed with a belt 22 and a plurality of interconnected modules 24, 26, 28, 30 and 32. The belt 22 is adjustable to a size necessary to fit around a body part such as the chest. The belt 22 is stretchable and encircles onto itself with a buckle 34. The modules 24-32 are connected to each other in a flexible, non-stretchable manner so as to form an articulated modular portion wherein the modules can lie against the skin with EKG electrodes contacts (not shown) that snap fit into connectors 36.1, 36.2 and 36.3.

The modules 24-32 are made of plastic housings with resilient flexible silicone rubber sleeves 38, being affixed to and placed between them to protect connecting webs and prevent access to electrical circuits.

Electrical access to the microprocessor is obtained by way of three individually-covered connector ports, 40.1, 40.2 and 40.3, not shown in FIGS. 1-5, but see FIG. 6. The electrical connection is made through releasably-hinged covers 42.1, 42.2 and 42.3 (see FIGS. 3 and 10) through which connections can be made with connectors 40.1, 40.2 and 40.3. Two respiration modules are used in case one fails.

A removable display 43 can be connected directly to port 40.2 to display pulse rate and respiration rate with conventional liquid crystal displays. The display 43 is provided with a clip 44 for attachment to a lapel or the like while the portable belt monitor 20 is being used. Pulse, respiration, and other alarm conditions are transmitted by an rf transmitter in module 26 to a remote receiver/monitor 45. This includes a receiver that is matched to the transmitter and further provides appropriate decoding networks to determine what type of alarm condition is being sent from the portable belt 20. The receiver/monitor 45 provides both visual and audible alarm indications.

A normally disconnected programming device 46 is provided to enable a physician to program alarm limits into a non-volatile memory in module 28 as well as read out contents of this memory. A printer 47 is included as part of device 46 to enable a visual examination of a patient's physiological parameters such as respiration and heart rate for a short time interval before and after an alarm condition arose.

With reference to FIGS. 4 and 6, module 24 includes a connector port 36.1 for an EKG electrode and a respiration transducer 48.1. Module 26 includes a transmitter 50 and audible alarm 52, module 28 a microprocessor 54 and part of an EKG sensor, and module 30 a battery 56. Module 32 includes connector port 36.3 for an EKG sensor and a second respiration transducer 48.2.

The modules 24-32 are each formed with rigid generally flat plastic housings 60.1-60.5 with side-located slots 62, see FIG. 8, through which webs such as 64, 66 extend to form a flexible articulated belt monitor 20. Webs 64 are each formed of substantially non-stretchable woven cloth whose ends are looped and stitched along transverse lines such as 68, see FIGS. 7 and 9, to receive metal holding rods 70.

The housing 60.2, 60.3 and 60.4 have web rod retainers 72 which are formed with recesses 74 sized to snugly receive the rods 70 and capture them with a strong frictional fit. Flexible and resilient connecting sleeves 38 engage peripheral slots 80 in the housing 60 so as to enclose the webs 64 and the spaces between modules. The sleeves 38 are glued to the housing 60 and may be formed of silicone rubber.

The end modules 24, 32 are terminated at belt buckles 34, 34' with rods 70' engaged in appropriate recesses 81. Buckle 34' has an end loop 82 through which a permanent loop connection is made to belt 22.

As shown in FIG. 11, buckle 34 is formed of two separable clips, a female end 84 that is connected to a web 66 and a male end 86 that is connected to belt 22. Releasable latching elements 90 in male end 86 engage complementary edges 92 in female end 84 while depressable levers 94 are used to disengage the elements 90 from ends 92.

Female end 94 has a central sealed switch 98 that is actuated by a member 100 in male end 86 when buckle 34 is closed. The actuation of switch 98 initiates operation of the belt monitor 20 by sending an appropriate start signal to the microprocessor in module 28 along a flexible conductor band 102.1.

The conductor band 102.1 (see FIG. 6) is part of a flexible conductor structure 104 that extends between the modules 24–32 with different flexible bands 102.2, 102.3 and 102.4 formed with various conductors, as appears necessary. These conductors between modules advantageously provide short EKG leads to modules 28 where the signals sensed by the electrodes are processed.

Breathing functions are detected with breathing sensors 48.1 and 48.2 that are respectively located in modules 24 and 32. Sensor 48.2 is shown somewhat enlarged in FIGS. 12–16. A sensor holder 110 is shown formed of a continuous looped flexible web 66. The web loop is joined at stitch lines 112 to form parallel panels 114, 116. Panels 114, 116 form a pocket 117 in which a piezoelectric pressure sensor 118 is mounted. Stitch lines 120 form the ends of web 66 into channels 122 to receive rods 70, 70' that mount in web rod retainers 72, 72'.

Piezoelectric sensor 118 can be formed of one but preferably a pair of parallel planar piezo elements 128, 130 respectively mounted on and electrically connected to conductive planar bendable but resilient metal substrates 132, 134. An insulator spacer 136 is placed between substrate 132 and element 130 and acts as a fulcrum against which elements 128, 130 are bent. A pair of peripheral bendable supports 140, 142 are affixed to the peripheral edges of substrates 132, 134 which seat on an edge 144 as illustrated in FIG. 16. A cut-out 146 is made in support 140 to accommodate electrical leads connected to substrate 132 and surface 148 of element 128.

The size of pocket 117 formed by web 66 is so selected that the sandwich structure formed by the elements, substrates, spacer and supports is snugly enclosed by panels 114, 116 when web 66 is placed in its operative position in belt 20 as shown in FIGS. 6, 12 and 13. Hence, when belt 20 is used and stretched to encircle a body, a belt tensioning occurs with forces in the directions as suggested by arrows 150, 152 in FIG. 14. These forces tend to reduce the width of pocket 117 by pulling on its sides so that the encircling panels 114, 116 introduce opposing forces as suggested by arrows 156, 158. Forces 156, 158 are substantially transverse to the tensioning forces in belt 20 at module 32 and parallel to the sensing axis of sensors 48.1 and 48.2. These forces cause peripheral supports 140, 142 that are in contact with panels 114, 116 to bend piezo elements 128, 130. When the tension decreases, the force arrows 150, 152 are either reversed or the forces reduced so that the panels allow the elements 128, 130 to return to a lower tension position.

Hence, the changes in elongationally directed tensions due to breathing are transformed into transversely-directed opposing forces. These cause a bending of elements 128, 130 which are so electrically connected, as explained with reference to FIG. 17, to produce a useful breathing signal for detection.

With a breathing sensor 48.2, unusual impacts and body motions do not produce significant signal levels. For example, an impact in only the direction of arrow 156 does not introduce the type of bending of piezo elements 128, 130 as caused by a change in the belt tension. Hence, the resulting signal output from the elements, 128, 130 is substantially smaller than that obtained from a belt tension change during breathing.

Further isolation of the breathing sensor 48.2 from extraneous impacts or body motions or from body resting positions is obtained by enclosing the sensor elements 128, 130 inside rigid housing 60.5. The housing is formed of a pair of separable segments 160, 162 which, when joined together as shown in the right side of FIG. 13, form a chamber that encloses the sensor elements 128, 130 with some clearance above and below web panels 114, 116. Laterally, as illustrated in FIG. 12, the peripheral supports 140, 142, snugly fit between posts 164 that are located in segment 160 and which are used to connect segments 160, 162 together with screws 166 as shown in FIG. 13.

FIG. 17 illustrates an electrical schematic for detecting breathing and heart rate functions. A microprocessor 180 is employed in module 28 and is programmed to monitor sensor signals to identify alarm conditions. Alarm outputs are generated and applied to a local audible alarm 182 as well as a remote rf alarm transmitter 184. Four alarm conditions are identified, a respiration rate problem, associated with a signal on line 186; a heart rate problem, identified by a signal on line 188 and a low battery signal on line 190. A poor contact, pc, condition of the cardiac electrodes is identified by producing signals on both lines 186 and 190 at the same time.

Transmitter 184 is a standard rf transmitter capable of responding to the alarm conditions on lines 186–190 to produce appropriate rf transmissions for decoding at a remote receiver, not shown, and subsequent alarm generation.

Respiration rate is obtained with parallel connected sensors 48.1 and 48.2. Each sensor is connected by leads such as 194 and 196 so that in response to opposing forces 156, 158 a mutual bending of piezo elements 128, 130 occurs either towards or away from each other, and an output voltage is produced on lines 198, 200. This output voltage is the result of an additive polarity of the output voltage from each element 128, 130. When the elements 128, 130 are bent in the same direction, as may occur in response to a single force 156 or 158, the voltages produced by the elements 128, 130 tend to cancel out.

Since sensors 48.1 and 48.2 are mechanically in "series" in belt 20, they are exposed to the same tension changes and thus can be connected in parallel as shown. A preamplifier produces an output on line 202 where a level detector 204 together with a threshold signal generator 206 produces a breathing signal on line 208 when the amplifier out exceeds the threshold.

Since the sensors 48 are quite sensitive to axial belt tension changes, they also respond to such small motions as produced from higher frequency heart beats. These, however, are excluded from the breathing signal on line 208 by employing an appropriate capacitor filter in the detector 204. The breathing signal on line 208 is in the form of pulses 209 whose repetition rate represents the breathing rate of the person wearing the belt. The leading edge 212 represents an inspiration or an expansion of the chest or abdomen while the trailing edge 214 represents a contraction or expiration. Breathing rate is measured from expansion to expansion or between successive leading edges 212, though trailing edges 212 could be used. The breath pulses are applied to an input bus of microprocessor 180, which in turn causes an LED 210 in module 26 (see also FIG. 6) to flash with each breath.

A heart signal is produced as shown in FIG. 17 with replaceable EKG electrodes 220.1, 220.2 and 220.3 that are inserted in connector ports 36.1 through 36.3. Electrodes 220 are provided with conventional conductive jelly to assure good electrical skin contact as belt 20 snugly encircles a body. One electrode, 220.3, serves as a reference electrode that is connected to circuit ground.

After appropriate amplification of electrode signals on lines 221.1 and 221.2 in amplifiers 222, the electrode signals C and D detected by electrodes 220.1 and 220.2 are coupled to a differential amplifier 224 whose output 226 presents an analog EKG signal. Various gains can be selected for amplifier 224 to accommodate different patients. Such gains are set with the programmer 46 (See FIG. 1) so that the analog EKG signal falls within an acceptable range. This gain setting is stored in a permanent memory associated with microprocessor 180.

A reference detector 228 senses and stores an amplitude value of the primary pulse of the cardiac signal that is on line 226, for example the initial pulse of each cardiac signal, and produces that on output 230. An integrator 231 is used whose maximum output is produced by integrating the positive going cardiac pulses on line 226. The reference signal becomes a reference against which the presence of subsequent EKG signals are detected by a comparator 232. The reference signal is allowed to slowly decay in a linear decreasing manner by discharge through a network 234. The reference detector can be a peak detector circuit that detects a predetermined percentage value of the maximum peak of the cardiac signal, for example, about 70 percent, though other values can be used.

Since normal physical behavior, such as a user hitting an electrode, can cause an EKG signal to increase to a level where the amplifier 224 would saturate and subsequent heart pulses be missed, the maximum excursion of the reference level between successive EKG signals is limited by a limiter network 236. This prevents the reference level online 230 from responding to sudden large EKG signal changes. In practice, excursions of the reference level are limited to about 30 percent of the reference level attributable to the previous EKG signal. In this manner repetitive heart pulses are amplified and sporadically generated pulses are ignored.

The comparator 232 produces an output pulse on line 240 each time the amplitude of the EKG signal on line 26 exceeds the reference level on line 230.

A network 250 is used to monitor the contact resistance between electrodes 220 and the skin by using a small (of the order of 22 nanoamps) DC current. The contact resistance can vary substantially during use of belt 20. Network 250 applies the reference signal on line 230 through high impedances 252 (about 22 megohms) to electrodes 220.1 and 220.2 and to the input 254 of an impedance reference network 256.

The latter's input is coupled to ground by a reference impedance 260. The value of this is selected commensurate with the maximum impedance or resistances 264.1 and 264.2 that can be respectively tolerated between electrodes 220.1, 220.2 and ground.

Amplifiers 266.1 and 266.2 are connected to electrode output lines 221.1 and 221.2 to generate contact signals that represent the quality of the skin contact of electrodes 220.1 and 220.2 If the contact resistance of either electrode is high, representative of a poor contact, the corresponding amplifier output 268.1 or 268.2 are large. After comparison with the reference contact signal on line 270 by differential amplifiers 272.1 and 272.2, a contact signal is produced on the output 274 of differential amplifier 276. This signal is applied to microprocessor 180 which is programmed to identify it as a poor contact (pc) signal.

The start of operation of microprocessor 180 is initiated with a closure of buckle 34. This causes a closure of normally open switch 98 (see also FIG. 11) whereby the DC battery 56 is connected to power the circuit shown in FIG. 17. A signal indicative of start-up power is obtained through a second pole 280 of switch 92 and applied on line 282 to reset and initiate operation of the microprocessor 180.

Battery power is monitored and a low level identified by a low level, low current requiring, detector 284. A low battery indicating signal is applied on line 285 to microprocessor 180.

Microprocessor 180 is driven by an oscillator/clock source 286 and has a random access volatile memory 288 as well as an erasable non-volatile memory 290 such as provided by an EEPROM. The RAM memory includes a so-called running memory 292 in which a history of functions is maintained for a minimum time period or for a predetermined number of measured physiological functions.

For example, as the program in microprocessor 180 runs through its cycle, values of respiration and/or heart rate are produced. These functions are recorded in RAM volatile memory 292 for a number of cycles that is equivalent to a minimum time of say one or several minutes.

When an event such as too low a heart rate is detected, all of the currently stored values in the running memory 292 is automatically and immediately permanently stored in the non-volatile memory 290 together with the particular event that caused it. In this manner, a history of a patient's critical functions is preserved to assist a physicians analysis of the event itself.

Figure 18:
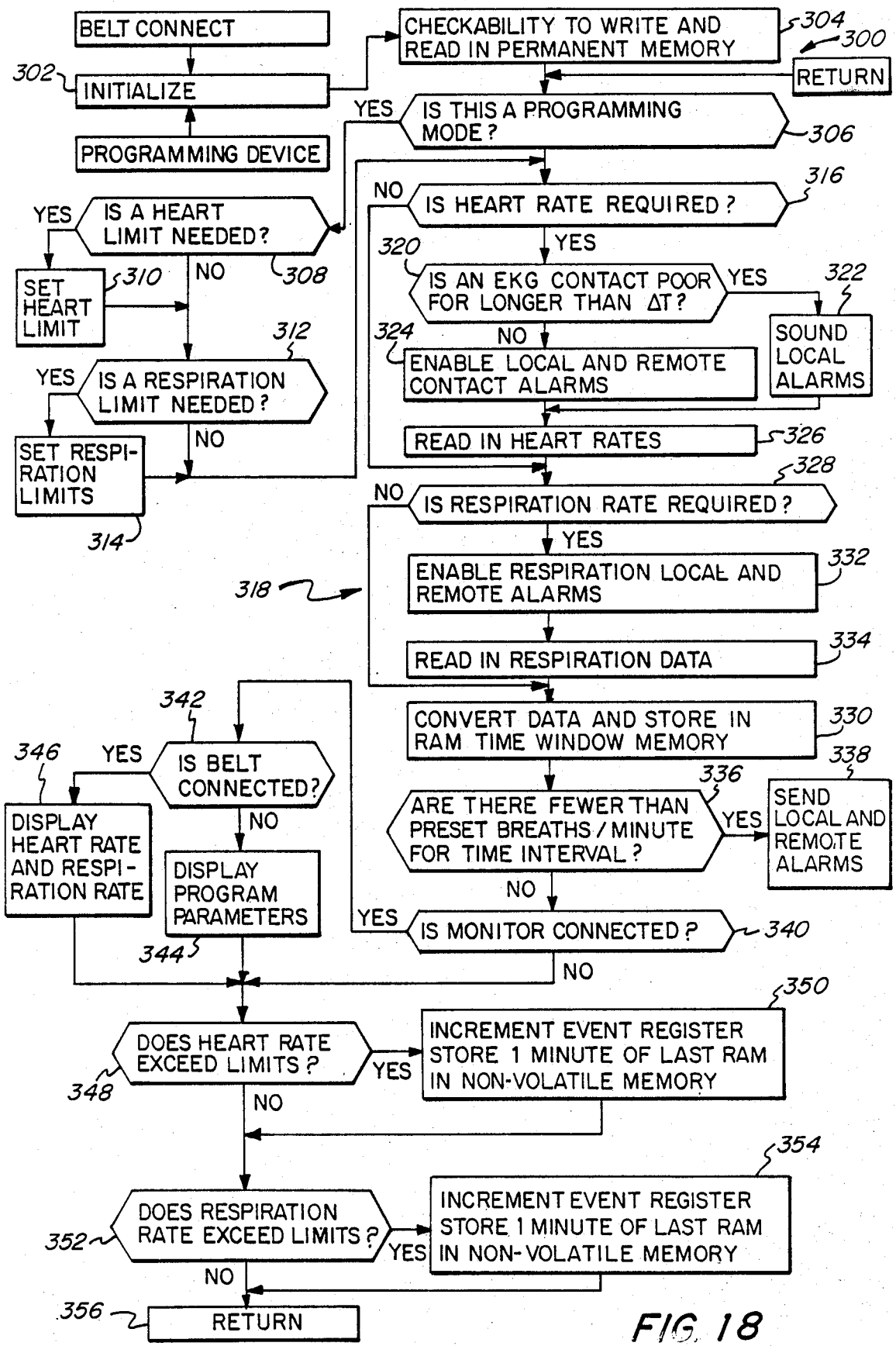
FIG. 18 is a flow chart illustrating a typical program for operating the microprocessor used in the belt monitor.

The microprocessor 180 also is provided with a data port 42 through which it can be programmed with alarm levels and such other functions as described with reference to FIG. 18.

The programming of microprocessor 180 can be done in different ways. The steps outlined in program 300 in FIG. 18 are illustrative.

At 302 an initialization process is implemented with which the program flags, values and registers are reset. This step can occur in response to an engagement of buckle 34, the signal on line 282 in FIG. 17, or by way of a remote programming device acting through a data port 42.

Step 304 checks the memories including the ability to write into and read the permanent memory 290. If an error or defect is found, an alarm is sounded, both for the local alarm and the rf remote monitor.

At 306 a check is made whether the system is to function in a program mode during which a physician can set alarm levels with the programming device 46, see FIG. 1. If so, a test is made at 308 whether heart limits are needed, which are set at 310 if needed. Otherwise a test at 312 is made whether respiration limits are needed. If so, the desired respiration limits are entered at 314 and a return is made to step 316.

The programming of alarm limits is done with a controller 46 as shown in FIG. 1 and which is connected to microprocessor 100 through one of its data ports 40.

A doctor prescribes the use of belt 20 for one of his patients. To program belt 20 with the patient's limits, the programmer 46 (see FIG. 1) is turned on and connected to an unbuckled belt 20. This automatically turns belt 20 "on" and shows the previously set alarm limits. Reprogramming of belt 20 to new limits involves actuating a set button 317.1 causing the old limit to disappear and dashes to be shown. A new limit is inserted, using a numerical keyboard. Once the correct limit appears on the display the physician pushes an enter button 317.2 and the display goes blank. The new limit is sent to belt 20, and if it is an acceptable number, the limit will reappear on the display; otherwise a series of dashes will be shown to indicate that the number was beyond the proper range, and a new number should be inserted. The physician may want to mute the local belt alarm 182 (see FIG. 17). This can be done by pressing an alarm mute button 317.3. In response an alarm mute dart on the display will turn on. All limits are programmed in this manner.

At 316 a check is made whether heart rate functions are to be monitored by investigating the presence of heart rate alarm levels. If not the program is advanced to a respiration segment 318. If so, a test is made at 320 of line 274 (FIG. 17) whether the heart electrodes make good contact for longer than a predetermined minimum interval, delta T for example, ten seconds. If so, the local alarm 182 is enabled and activated at 322. If not, the local and remote alarm are enabled at 324 and the presence of heart pulses on line 240 is noted at 326 to determine the interval durations between successive pulses. Techniques for measuring such intervals are well known and typically may include one or more registers driven by a clock of known pulse rate. The number of clock pluses between heart pulses then is indicative of the heart rate. In a preferred mode, heart rate is calculated by measuring the time between three heart successive heart beats.

At 328 a check is made whether respiration is to be monitored. This as with the heart test 320 can be done by testing for the presence of respiration alarm limits. If not, the program is advanced to step 330, but if so, the respiration local and remote alarms are enabled at 332 and respiration pulses on line 208 in FIG. 17 are identified and the intervals between successive pulses is measured at 334.

At 330 the measured heart and/or respiration intervals are converted to rate measurements that are in the same units as the alarm limits, typically heart beats per minute and apnea time in seconds are used, and the converted values stored in the running memory. A test is made immediately at 336 whether the respiration rate is less than a preset absolute value for more than a predetermined time. This test is made to provide an absolute lower limit for respiration. If the test result is positive an alarm, both for local and for remote, is set off at 338.

At 340 a test is made whether the portable visual monitor 43 is connected to one of the ports 42 (see FIG. 1). If so, a further test is made at 342 whether the belt buckle 34 is open or closed. If open, the program assumes that an analysis is being made and displays program parameters at 344. If closed, the heart and respiration rates are displayed at 346 in monitor 43. Note that the act of connecting the monitor 43 to belt 20 can activate it as shown at 347.

A test is then made at 348 whether the last measured heart rate exceeds limits, namely, whether it is below a minimum rate or above a maximum rate. If so, an event register is incremented at 350 and the contents of the running memory 292 (FIG. 17) are stored into the non-volatile memory 290 (FIG. 17), together with data for a selected number of subsequent readings, typically for about 50 seconds.

At 352 the last respiration measurements is compared with associated alarm limits, i.e., whether the interval is below a minimum or above a maximum limit. If any one is exceeded, the event register is again incremented at 354 and the contents of the running memory and subsequent data stored in the non-volatile memory to provide a permanent record of a patient's functions for a short time leading to and after the event. Each time an event occurs, such as a respiratory or a heart rate problem, a local alarm is sounded and an rf transmission is made to the remote receiver/monitor 45. This then produces both an audible as well as visual alarm. Audibly distinctive alarms are used.

A return is then made at 356 to step 306.

Having thus described a preferred embodiment, its advantages can be appreciated. Variations can be made without departing from the scope of the invention as set forth in the following claims. For example, some of the electrical network functions can be performed by the microprocessor. In such case, it may be necessary to use a digital to analog converter to obtain digital values of the respective heart and/or respiration measurements. Different breathing sensors 48 can be used such as variable inductance coils through these devices may present too much of a current drain.

What is claimed is:

1. A physiology monitor for sensing body respiratory functions, comprising:
   a belt adapted to fit on a body so as to undergo tension changes due to body expansion and contraction during breathing;
   said belt having first sensing means with a preferential sensing axis for producing a breathing signal in response to opposing forces along the sensing axis; and
   holder means interposed in the belt as part thereof to operatively hold the sensing means with its sensing axis aligned generally transverse to tension in the belt and for transforming a tension change in the belt at the sensing means to opposing forces directed along the transverse sensing axis to produce said breathing signal.

2. A physiology monitor as claimed in claim 1 wherein the holder means comprises a strip of fabric material shaped so as to form a pair of adjacent panels that define a pocket between them; said sensing means being inside the pocket and said fabric material having ends affixed so as to tend to reduce the width of the pocket when tension in the belt increases due to respiratory inhalation.

3. A physiology monitor as claimed in claim 2 wherein the sensing means comprises a pair of generally flat piezoelectric elements and a fulcrum placed between the elements so as to bend the elements towards each other when the pocket width tends to be reduced by an increase in belt tension, said elements being interconnected so as to produce a breathing signal that is insensitive to changes in temperature.

4. A physiology monitor for sensing body respiratory functions, comprising:
   a belt adapted to fit on a body so as to undergo tension changes due to body expansion and contraction during breathing:
   said belt having first sensing means with a preferential sensing axis for producing a breathing signal in response to opposing forces along the sensing axis;
   holder means interposed in the belt as part thereof to operatively hold the first sensing means with its sensing axis aligned generally transverse to tension in the belt and for transforming a tension change in the belt at the sensing means to opposing forces directed along the transverse sensing axis to produce said breathing signal; and
   a rigid enclosure around the sensing means and at least partially around the holder means to enhance isolation of the sensing means from external impacts occurring along the sensing axis while enabling the sensing means to remain sensitive to belt tension changes due to breathing.

5. The monitor as claimed in claim 4 wherein the holder means comprises:
   a flexible material that has a collapsible pocket with sides, said pocket sides being anchored to the belt, and said pocket containing said sensing means and being effectively freely mounted inside the rigid enclosure.

6. The monitor as claimed in claim 5 wherein the sensing means comprises:
   a pair of parallel mounted spaced-apart planar piezoelectric elements mounted inside said pocket, said planar elements being aligned with their planes generally parallel to the belt at the sensing means while producing electric signals in response to tension changes in the belt.

7. The monitor as claimed in claim 6 and further including:
   means for connecting the piezoelectric elements so that the polarity of signals respectively produced thereby from belt tension changes electrically add, while electrical signals attributable to temperature variations electrically tend to cancel, so as to reliably generate said breathing signal in response to belt tension changes attributable to breathing.

8. The monitor as claimed in claim 7 and further comprising:
   means for removing portions of the breathing signal attributable to heart beats.

9. The monitor as claimed in claim 7 wherein the pocket has opposite panels which tend to move towards each other when opposite ends of the panels are pulled away from each other and further including a fulcrum spacer mounted between the piezoelectric elements so as to cause a bending thereof towards each other when the panels are moved towards each other by an increase in tension in the belt.

10. The monitor as claimed in claim 9 and further including:
    means for monitoring the breathing signal to detect a breathing anomaly and produce an alarm signal indicative thereof.

11. The monitor as claimed in claim 10 and further comprising:
    means for transmitting the alarm signal; and
    battery means for providing electrical power to said sensing means, said means for monitoring and said means for transmitting to form a self-contained portable respiration sensor.

12. The monitor as claimed in claim 4 and further including:
    a second, a said sensing means, a said belt holder means and a said rigid enclosure, displaced along the belt from the first sensing means, said second sensing means producing a second breathing signal, and means for combining breathing signals from the first and second sensing means so as to assure an output signal representative of breathing of the body when a said sensing means fails to provide a breathing signal.

13. A belt adapted to fit on a patient for monitoring a physiological function, comprising:
    a plurality of mechanically, articulatively-connected and electrically connected, generally flat modules that are distributed so as to cover different portions of the patient, selected, spaced-apart modules being each provided with respiration sensing means for generating a breathing signal in response to belt tension changes attributable to breathing;
    said respiration sensing means having a preferential sensing axis for producing a breathing signal in response to opposing forces along the preferential sensing axis; and
    holding means interposed with the modules in the belt as part thereof to hold the sensing means within a said module with the sensing axis aligned generally transverse to the belt at the sensing means and for transforming a tension change in the belt to opposing forces to produce a said breathing signal.

14. The belt as claimed in claim 13 wherein the sensing means comprises a pair of parallel mounted, spaced-apart piezoelectric elements mounted in said holding means to bend towards each other in response to opposing forces produced by tension in the belt; and
    means for connecting the piezoelectric elements so that the polarity of signals respectively produced thereby from belt tension changes electrically add, while electrical signals attributable to temperature variations electrically tend to cancel, so as to reliably generate said breathing signals in response to belt tension changes attributable to breathing by the patient.

15. The belt as claimed in claim 14 wherein the holding means includes flexible webs which have collapsible pockets with sides, said pocket sides being anchored to a portion of the belt so as to be a part thereof, with respective pockets containing a said sensing means.

16. The belt as claimed in claim 15 wherein the modules containing said sensing means comprise rigid enclosures that freely receive the pockets, said enclosures having side-located slots through which said flexible webs extend for anchoring to the belt.

17. The belt as claimed in claim 16 and further comprising:
    means located in a said module for monitoring the breathing signals from the respiration sensing means in the spaced-apart modules and generating an alarm signal when a breathing anomaly occurs;
    means for transmitting said alarm signal to a location that is remote from the patient; and battery means for providing electrical power to the monitoring means and transmitter means to render said belt portable.

18. A physiology monitor for sensing body respiratory functions, comprising:
a belt adapted to fit on a body so as to undergo tension changes due to body expansion and contraction during breathing;
said belt having sensing means with a sensing axis for producing a breathing signal in response to a force along the sensing axis;
holder means for holding the sensing means and interposed in the belt as part thereof to transfer a change in belt tension to a force along the sensing axis to produce said breathing signal; and
a rigid enclosure around the sensing means and the holder means to enhance isolation of the sensing means from external forces directed along the sensing axis so as to reliably produce said breathing signal from changes in belt tension.

19. The monitor as claimed in claim 18 wherein said belt has first and second of said sensing means, said first and second sensing means being spaced apart along the belt, with first and second of said holder means respectively holding the first and second sensing means and with first and second of said rigid enclosures respectively placed around said first and second sensing and holding means, and means for combining breathing signals from said first and second sensing means.

* * * * *